United States Patent
Phelps (10) Patent No.: US 6,221,048 B1
(45) Date of Patent: *Apr. 24, 2001

(54) NEEDLE DEVICE

(76) Inventor: David Y. Phelps, 2815 Stratford Ave., Louisville, KY (US) 40207

( * ) Notice: Subject to any disclaimer, the term of this patent is extended or adjusted under 35 U.S.C. 154(b) by 0 days.

This patent is subject to a terminal disclaimer.

(21) Appl. No.: 09/179,708

(22) Filed: Oct. 27, 1998

Related U.S. Application Data (62) Division of application No. 08/643,470, filed on May 6, 1996, now Pat. No. 5,827,221, which is a continuation of application No. 08/361,982, filed on Dec. 22, 1994, now Pat. No. 5,514,111, which is a division of application No. 08/057,354, filed on May 3, 1993, now Pat. No. 5,376,082, which is a continuation-in-part of application No. 07/788,253, filed on Nov. 5, 1991, now Pat. No. 5,207,647.

(51) Int. Cl.$^7$ ................................................. A61M 5/178
(52) U.S. Cl. .............................. 604/164.12; 604/167.03; 604/158; 604/246; 604/506
(58) Field of Search ...................................... 604/164, 167, 604/158, 274, 256, 248, 246, 28, 49, 51, 500, 506, 507, 164.01, 164.12, 167.03

(56) References Cited

U.S. PATENT DOCUMENTS

| 4,654,030 | * | 3/1987 | Moll et al. ............................. 604/165 |
| 4,902,280 | * | 2/1990 | Lander ................................. 604/165 |
| 4,931,042 | * | 6/1990 | Holmes et al. ....................... 604/164 |
| 5,116,353 | * | 5/1992 | Green .................................. 604/184 |
| 5,207,647 | * | 5/1993 | Phelps ................................. 604/158 |
| 5,376,082 | * | 12/1994 | Phelps ................................. 604/248 |
| 5,514,111 | * | 5/1996 | Phelps ................................. 604/248 |

* cited by examiner

Primary Examiner—Ronald K. Stright, Jr.
(74) Attorney, Agent, or Firm—Don Halgren

(57) ABSTRACT

A needle device for the delivery of medicaments, insuflation or other medical devices, having a reciprocable needle sensitive to lack of resistance, whereupon such needle retracts, permitting a cannula therewith to provide access to the penetrated body.

19 Claims, 6 Drawing Sheets

NEEDLE DEVICE

This application is a Divisional of Ser. No. 08/643,470 filed May 6, 1996 now U.S. Pat. No. 5,827,221; which is a Continuation of Ser. No. 08/361,982 filed Dec. 22, 1994 now U.S. Pat. No. 5,514,111; which is a Divisional of Ser. No. 08/057,354 filed May 3, 1993 now U.S. Pat. No. 5,376,082; which is a Continuation-In-Part of Ser. No. 07/788,253 filed Nov. 5, 1991 now U.S. Pat. No. 5,207,647.

BACKGROUND OF THE INVENTION (1) Field of the Invention

This invention relates to needle devices, and more particularly to medical devices for introducing a needle and/or catheter into a body cavity a patient.

(2) Prior Art

The present application incorporates by reference my co-pending application, Ser. No. 07/788,253, filed Nov. 5, 1991 no U.S. Pat. No. 5,207,647.

A veress needle has a hollow, blunt inner needle, spring loaded, within a larger piercing cannula, to permit entry into a body space without laceration of obdominal structures. Several patents which disclose such devices are as follows:

U.S. Pat. No. 5,139,485 to Smith et al, which shows a spring loaded with an acoustic alarm to indicate passage of the needle into a space in a body.

U.S. Pat. No. 5,104,381 to Gresl et al, with a viewable indicator on a stylet to indicate penetration.

U.S. Pat. No. 5,098,388 to Kulkashi et al, having a porthole for receiving a fluid coupling permitting fluid to be passed into the needle.

BRIEF SUMMARY OF THE INVENTION

The present invention provides a needle device which, when cocked, permits penetration of its distal tip into a body until it senses a space or void. The tip, which is a needle, is then retracted automatically and locked within the device, preventing further cutting capabilities of that trocar.

The present invention comprises a needle device having an elongated housing. The housing has a proximal and a distal end. An opening is arranged through the proximalmost end of the housing. A carriage shaft is disposed within the housing and extends slightly outwardly of the proximal opening.

An elongated cannula is attached to the distal end of the housing through a hub. The distalmost end of the cannula has a tip thereon. A needle is slidably disposed through the cannula. The distal end of the needle has a pointed tissue piercing tip. The proximal end of the needle (or trocar) is engaged with a detent assembly arranged at the distal end of the carriage shaft. The needle is hollow, allowing an endoscope (fiber optic camera) or other device to be place therethrough.

A first compressive spring is arranged within the housing to provide a proximally directed bias onto the carriage shaft. A second compressive spring is arranged within the housing, about the proximal end of the needle, but which spring has less force than the first spring. The distal end of the second spring keeps a forwardly or distally directed bias upon a flange on the needle. The proximal end of the second spring engages the distal end of the carriage shaft. The needle has a proximally extending finger or link which engages a detent assembly. The link rotates the detent assembly to effectuate rearward retraction of the carriage shaft and the needle with respect to the housing.

A valve in the proximal end of the cannula or catheter, is coaxial therewith, and is disposed within a cap and base assembly. Opon removal of the needle from the catheter, the cap and base assembly can be rotated with respect to one another, to open or close the valve therein.

The housing can be removed from the cannula/hub assembly to permit valvable access to the body space through the cannula. A stopcock is attached to the hub assembly to permit insuflation of a patient through the cannula. Insuflation is the pumping of carbon dioxide into a body (peritoneal) cavity to distent the fascis skin.

In operation of the present invention, the needle device is initially cocked by the attending physician, by pressing upon the proximalmost end of the carriage shaft. This causes the detent assembly to become engaged with the carriage shaft and compresses the first spring. The needle is also caused to extend outwardly slightly beyond the distal end of the cannula, causing the exposure of the cutting tip of the needle.

Penetration of skin, tissue and ligaments by gently force applied to the device into a patient, causes a slight rearward pressure and movement on the needle, simultaneously compressing the second spring and causing the link to move to a position that upon any forward motion of the needle link assembly, the link will rotate the detent assembly and thus release the carriage.

Upon entry of the needle into the body space, the needle is advanced distally very slightly by bias of the second spring thereagainst. This slight forward or distal advance of the needle causes the link attached to it to trip the detent assembly, thus releasing the carriage shaft from capture, whereupon the first, more powerful spring pushes the carriage shaft and attendently attached needle rearwardly or proximally, with an audible sound. This causes the needle to also be retracted proximally within the cannula. The proximal end of carriage shaft is also caused to extend out through the opening in the proximal end of the housing, to provide a visual indication of penetration into the body space, as well as the audible indication of such entry. A bore extends longitudinally through the carriage shaft, and is in communication with the bore in the needle. An optical device such as an endoscope, or a medicament supply may be disposed within such bore to permit visualization of the puncture and body organ and/or supply of medicaments therein.

Dissassembly of the cannula from the housing and opening of the bore of the catheter permits delivery of medicaments or other medical devices. The valve could be closed to close the bore through that cannula. A valved side port through the base permits the valve at the proximal end of the cannula to be closed (or open) while permitting supply of medicaments therethrough simultaneously with optics or other medicaments being disposed through the valve in the base.

It is apparent that this device may also be used to locate/enter other spaces or potential spaces in the body where there is less resistance than in the surrounding tissue, such as with the pneumothorax needles, drainage of absesses or the like.

BRIEF DESCRIPTION OF THE DRAWINGS

The objects and advantages of the present invention will become more apparent when viewed in conjunction with the following drawings, in which.

DESCRIPTION OF THE PREFERRED EMBODIMENT

Figure 1:
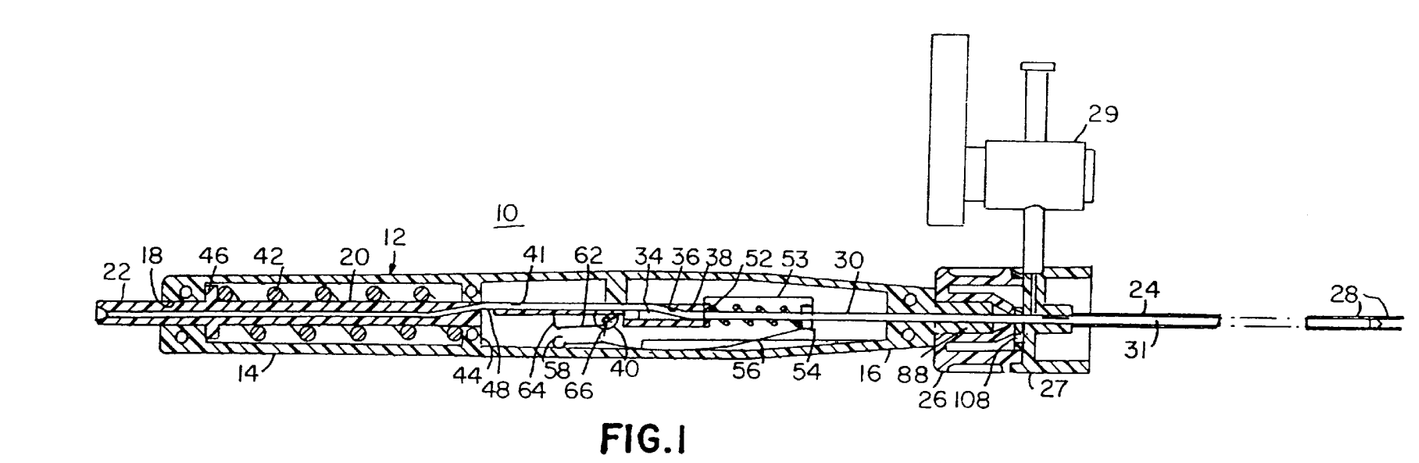
FIG. 1 is a side elevational view insection of an veress needle device in a "packaged" configuration.

Referring now to the drawings in detail, and particularly to FIG. 1, there is shown a veress needle device 10, having an elongated housing 12 having a proximal end 14 and a distal end 16. A proximal opening 18 is arranged through the proximal end 14 of the housing 12. A longitudinally slidable carriage shaft 20 is disposed within the housing 12, and has a proximal end 22 which extends slightly outwardly of the proximal opening 18, when the veress needle device is shown in its "packaged" or "shipping" configuration depicted in FIG. 1.

Figure 10:
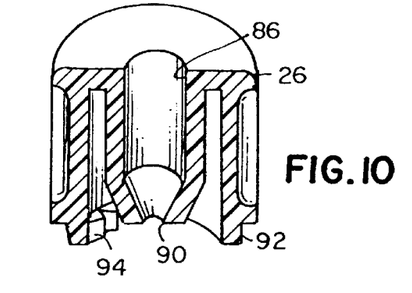
FIG. 10 is an enlarged longitudinal sectional view of the catheter cap.
Figure 11:
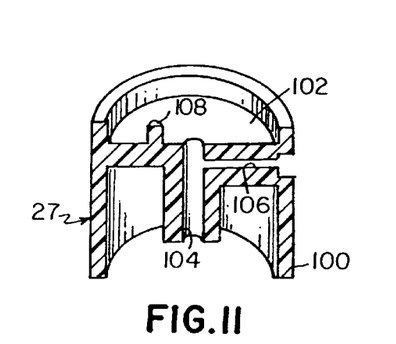
FIG. 11 is an enlarged longitudinal sectional view of the catheter base.

An elongated cannula (or catheter) 24 is attached to the distal end 16 of the housing 12 through a mating cap 26, shown in an enlarged sectional view in FIG. 10. The cannula 24 has a tip 28 on its distalmost end. A tubular needle 30 extending from the distal end 16 the housing 12 is slidably disposed within the lumen of the cannula 24. The needle 30 has a pointed tissue piercing tip 32 on its distalmost end. A discharge opening 33 is disposed proximally adjacent the tip 32, the opening 33 being in fluid communication with a lumen 31 in the tubular needle 30. A base 27 is arranged on the proximal end of the cannula 24. The base 27 has a central bore 104 which extends longitudinally therethrough and is in communication with the lumen 31 in the needle 30. A side valve 29 is attached to the side of the base 27 and is in fluid communication through a channel 106 with the bore 104, as shown in FIG. 11.

Figure 6:
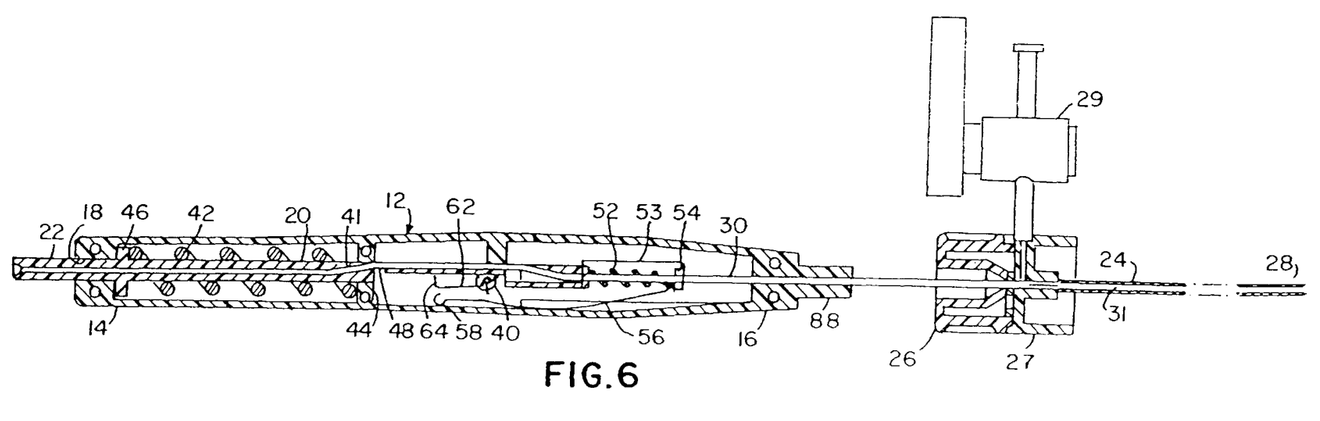
FIG. 6 is a view of the needle device being removed from its catheter tip.
Figure 6A:
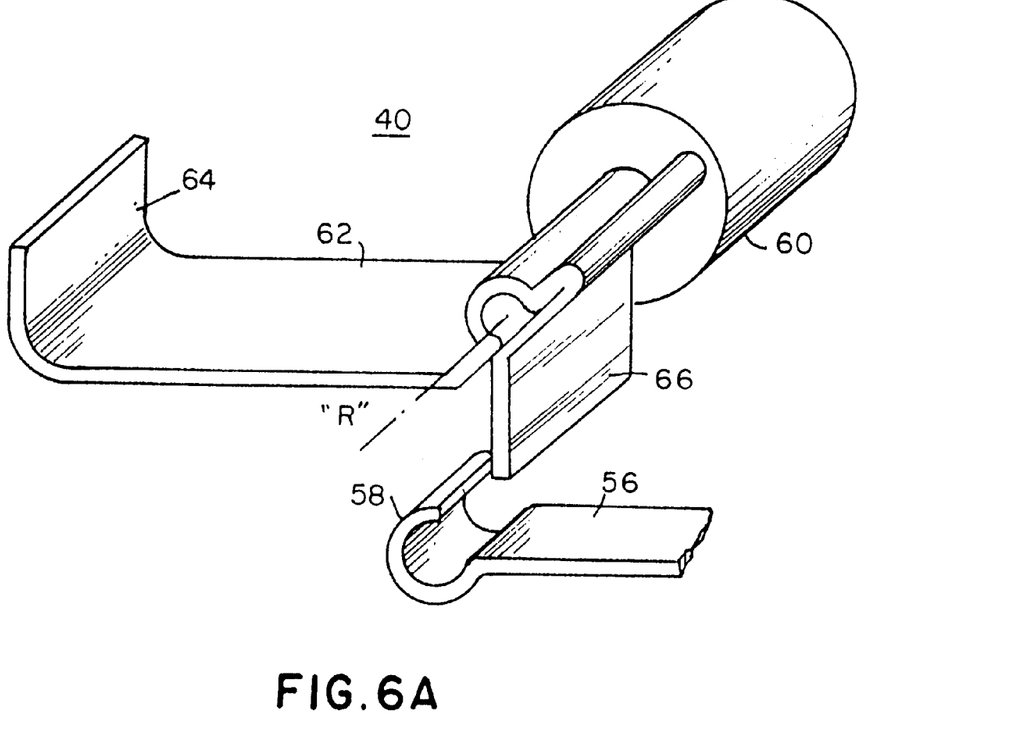
FIG. 6A is a perspective view of a detent assembly arranged within the housing of the veress needle.

The needle 30 has a proximal end 34 which extends into the distal end 16 of the housing 12 and which slidably engages a tapered channel 36 in a flange 38 on the distal end of the carriage shaft 20, which is adapted to facilitate engagement and disengagement of a detent assembly 40, shown more clearly in FIG. 6A.

A first compressive spring 42 is arranged within the housing 12 between an abutment 44 therein disposed about the carriage shaft 20 and an annular flange 46 secured to the carriage shaft 20 near its proximal end 22. The first compressive spring 42 provides a rearward or proximally directed bias onto the carriage shaft 20. A longitudinal bore 41 extends through the carriage 20, and is in fluid communication with the bore 31 of the needle 30.

A notch 48 is arranged transversely about the mid-point of the carriage shaft 20, as shown in FIG. 1.

A second compressive spring 52 is disposed about a portion of the proximal end 34 of the needle 30. The second spring 52 has a distal end which abuts an annular flange 54 which is disposed about the approximate mid-point of the needle assembly 30. The second spring 52 has a proximal end which is in abutting engagement with the distalmost end of the carriage shaft 20 and the flange 38 thereon. An elongated resilient finger or link 56 is attached to the flange 54 and extends rearwardly therefrom. The link 56 has a "J" shaped distalmost tip 58 which engages the detent assembly 40. A "U" shaped clip 53 has an end which engages the flange 38 and another end which acts as an abutment to the flange 54, this other end slidably receiving the needle therethrough.

Figure 7:
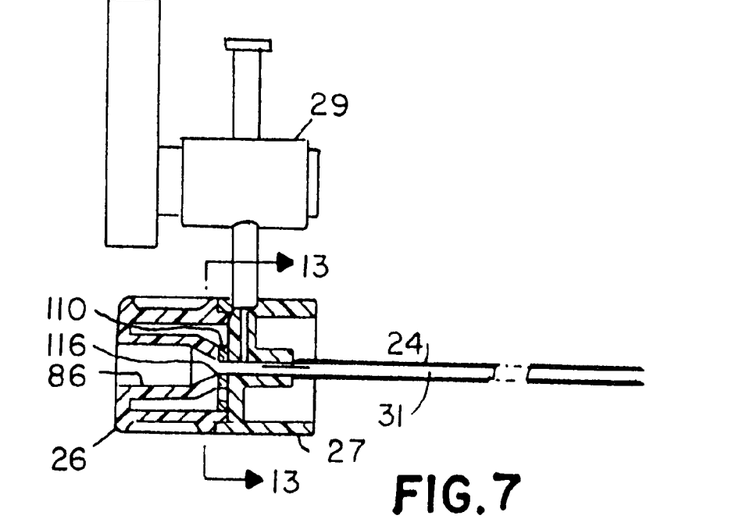
FIG. 7 is an enlarged longitudinal sectional view of the hub, base and cannule in a valve open orientation.
Figure 8:
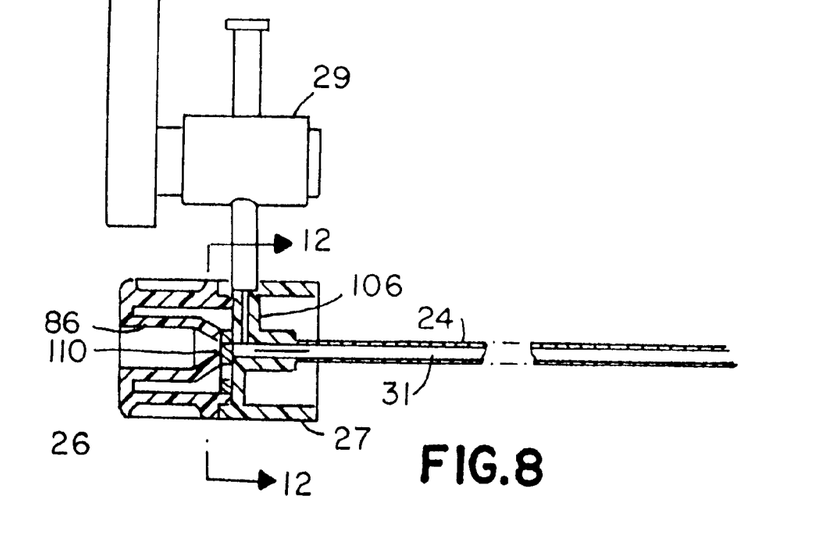
FIG. 8 is an enlarged longitudinal sectional view of the hub, base and cannula in a valve closed orientation.

The detent assembly 40, shown more explicitly in FIG. 6A, comprises a pivot hub 60 which is pivotably secured to an inside wall of the housing 12. The pivot hub 60 is of generally cylindrical configuration and has an an axial post, not shown, on which a spring leg 62 is fixed. The leg 62 has a distal toe 64 arranged at a right angle thereto. The toe 64 is arranged to engage the notch 48 on the carriage shaft 20. A release flange 66 extends from the proximal end of the leg 62, as shown in FIG. 7. The tip 58 of the link 56 is juxtaposed to engage and pull on the release flange 66 so that the toe 64 is pivoted from the notch 48, thus releasing the carriage shaft 20, in a manner descrbrd hereinbelow. 50 adjacent the shoulder 48 of the carriage shaft 20.

The distalmost tip 58 of the link 56 is arranged to mate with the toe 64 and give it a slight "pull" to cause it to rotate (counter clockwise as shown in the drawings) so as to lift the toe flange 64 from the notch 48 in the carriage shaft 20.

The cannula 24 has the mating cap 26 on its proximal most end, as shown in FIGS. 1–6. The cap 26, has a tapered central bore 86, which slidably mates with a tapered projection 86 on the distal end 16 of the housing 12. The cap 26 has an opening 90 at the distal end of the bore 86. An annular wall 92 defines the side peripheral surface of the cap 26. An angular array of gear teeth 94 are disposed on the inner peripheral surface of the distal end of the annular wall 92, as shown in FIG. 10.

A base 27, shown in FIGS. 1–6, but shown more clearly in section, in FIG. 11, comprises an annular wall 100 having a disc 102 molded adjacent its proximal end. The disc 102 has a central bore 104 arranged therethrough. A channel 106 is arranged through the wall 100 and is in communication with the bore 104. A pivot axis 108 extends proximally off of the disc 102 between the wall 100 and the bore 104.

Figure 9:
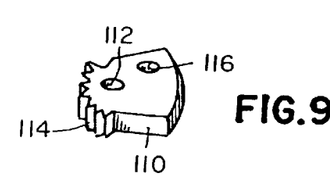
FIG. 9 is a perspective view of the valve member which rotatively mates with the base.

An elongated valve member 110, shown in cross-section in FIGS. 1–6, is shown in perspective in FIG. 9, has an opening 112 across one end thereof, which mates on the pivot axis 108 off of the disc 102 on the base 96. The valve member 110 has an arrangement of gear teeth 114 on one end adjacent its opening 112. The valve member 110 has an arrangement of gear teeth 114 on one end adjacent its opening 112. The valve member 110 has a circular second opening 116 on the other end thereof, the second opening being of a diameter similar to the opening 90 in the cap 26 and the central bore 104 in the base 27. The needle 30 is sized to slide through each of these openings when they are in longitudinal alignment, as is the case shown in FIG. 10.

In assembly of the cannula 24, the valve member 110 is mounted with its first end opening 112 on the pivot axis 108.

Figure 12:
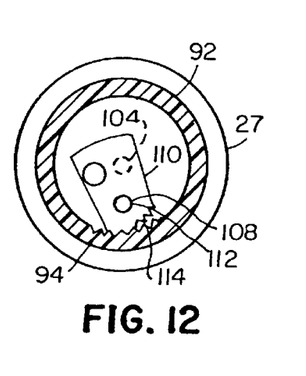
FIG. 12 is a view taken along the lines XII—XII of FIG. 8, with the needle removed and the valve closed.
Figure 13:
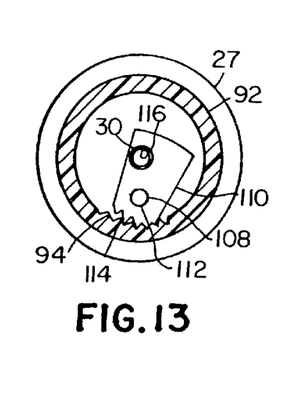
FIG. 13 is a view taken along the lines XIII—XIII of FIG. 7, and the valve opened.

The cap 26 then fits against the disc 102 with the distal lip of its walls 92 mating within the proximal lip of the walls 100 of the base 27, with the bore 90 in alignment with the second end opening 116 of the valve member 110 and the bore 104 of the base 27. The teeth 114 of the valve member 110 are engaged with the teeth 92 on the inner distalmost lip of the wall 92 of the cap 26. Once the needle 30 has been removed from the catheter 30, the valve member 110 may be arcuately pivoted about pivot axis 108 on the cap 27 by rotation of the cap 26 therewith, because of the interengagement of the gear teeth 114 and 94 therebetween. Such a movement of the valve member 110 is shown in FIGS. 12 and 13, where FIG. 12 indicates the position of the valve member 112, now closed, once the needle 30 has been withdrawn from the aligned openings 90, 116, and 104.

The side valve 29, shown in FIGS. 1–6, mates with the channel 106 in the base 96 to permit fluid communication with the bore 104 and the canulea 24, once the needle 30 has been withdrawn therefrom, permitting access to the body cavity therewith.

Figure 2:
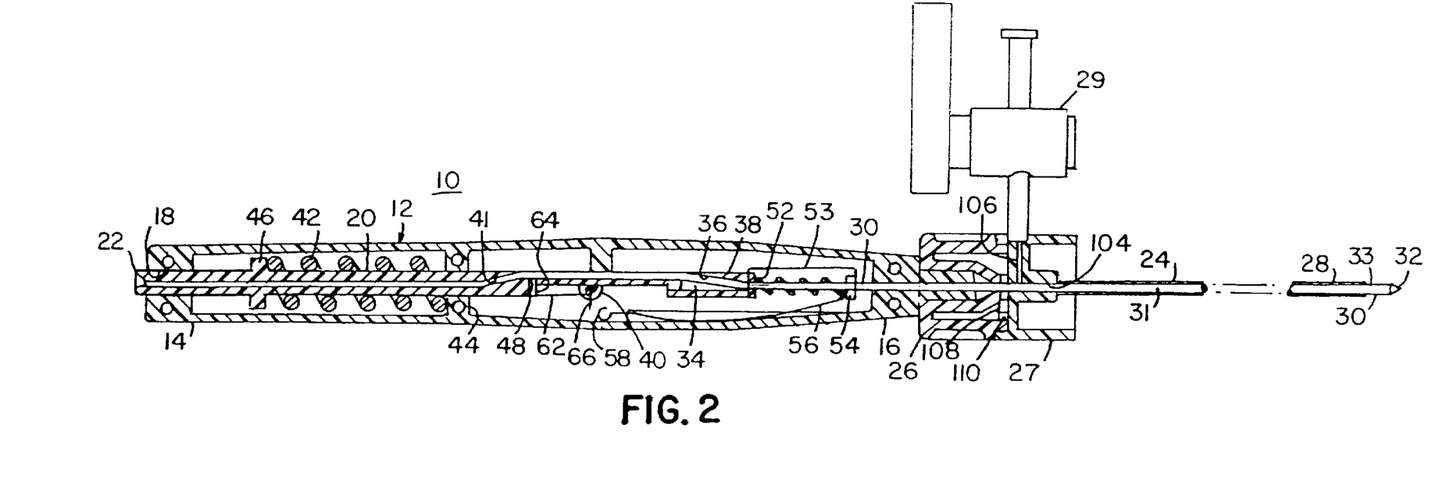
FIG. 2 is a view similar to FIG. 1, showing the veress needle device in its "cocked" configuration.

In operation of the needle device 10 the attending physician "cocks" it from its "packed" state shown in FIG. 1 to its "cocked" state by pressing the proximal end 22 of the carriage shaft 20 distally, or to the right, as shown in FIG. 2, thereby compressing the first spring 42 and bringing the notch 50 into mating engagement with the flange 72 of the outwardly biased U-shaped spring 64. The tip 32 of the needle 30 is also at this time, once the device 10 has been cocked, to be caused to extend about 2 mm. beyond the distalmost end of the cannula tip 28, and simultaneously permitting the cutting portion of the needle assembly 30 to be distally exposed.

Figure 3:
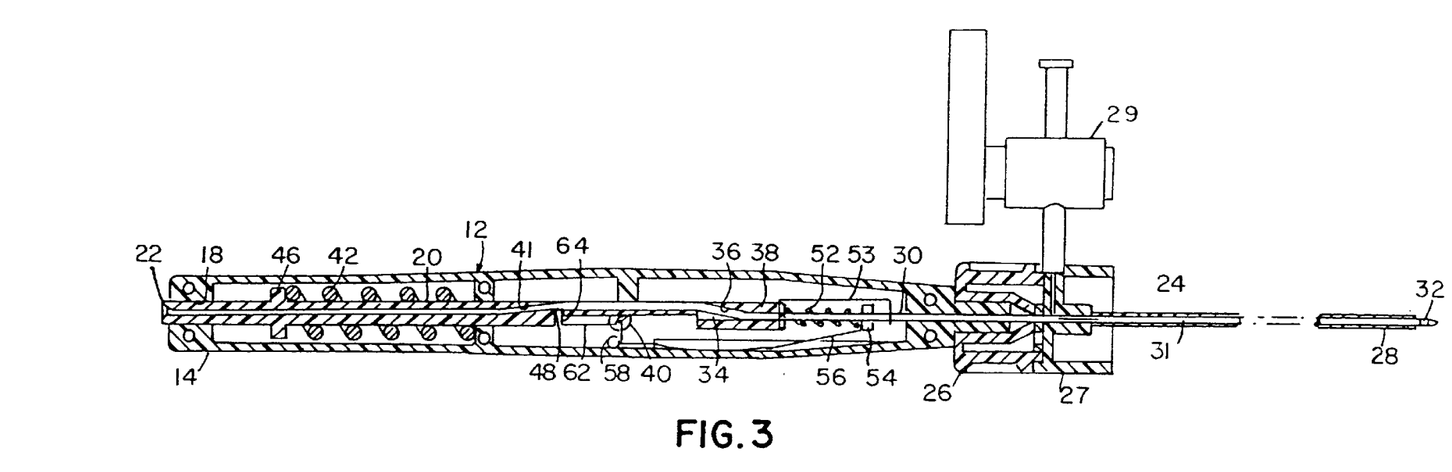
FIG. 3 is a view similar to FIG. 1, showing the veress needle device during penetration of tissue.

Gentle but constant pushing force by the physician on the needle device 10 penetrates the patient's skin, soft tissue and ligaments, and causes the needle assembly 30 including the link 56, to be pushed-back into the catheter 24 slightly, (to the left) as shown in FIG. 3, and also compressing the second compressive spring 52 slightly, and moving the tip 58 of the link 56 proximally past the pivot hub 60.

Figure 4:
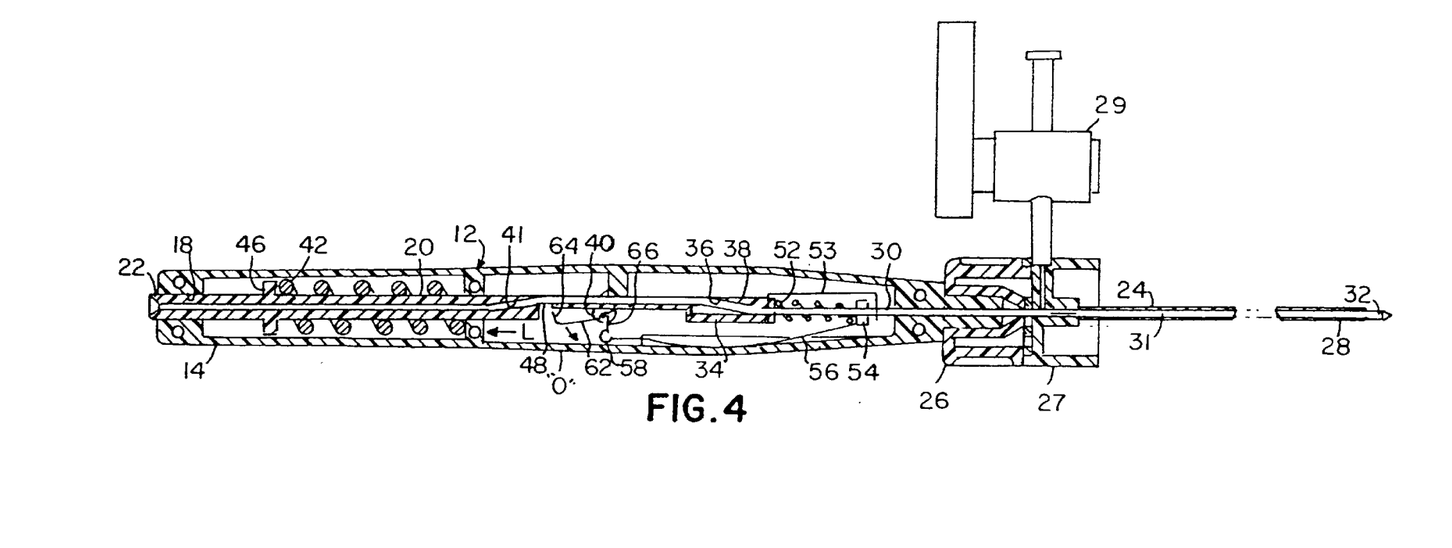
FIG. 4 is a view similar to FIG. 1, showing the veress needle device just as it enters an open space.

Upon entering a body cavity the needle 30 encounters less resistance, and is therefore caused to advance slightly, for this example about 0.25 mm. because of its forward (distally directed) bias from the second compressive spring 52 acting upon the annular flange 54 secured thereto, the needle 30 being shown thusly in FIG. 4. The distal tip 58 of the link 56 mates with the toe 64 extending off of the hub 60.

As the needle 30 advances for example, about 0.25 mm. upon meeting with sudden diminished resistance upon entering the epidural space it also causes the link 56 to advance forwardly a corresponding amount. The frontwardly moving (distal) end 58 of the link 56 having been engaged with the release flange 66 of the pivot hub 60, causes the pivot hub 60 to rotate slightly, about its axis of rotation "R", counter-clockwise as shown in the drawings, to cause the rotation of the leg 62 as well, lifting the toe flange 64 out from locking engagement in the notch 48 of the carriage shaft 20, as indicated by the arrow "O" in FIG. 4.

Figure 5:
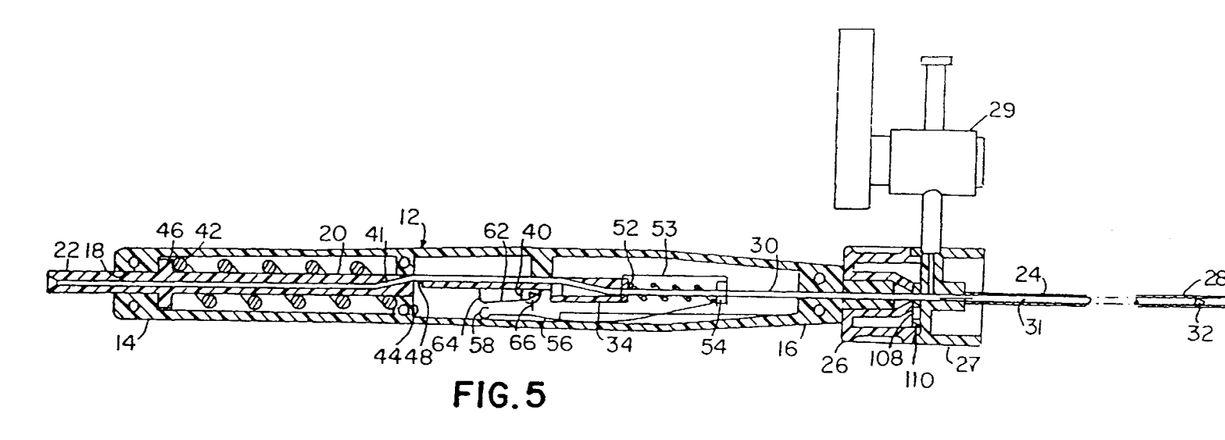
FIG. 5 is a view similar to FIG. 1, showing the veress needle device after it has entered the epidural space.

The first compressive spring 42, being stronger than the second compressive spring 52 is thus released, so as to push the carriage shaft 20 rearwardly, or the left, as shown in FIG. 4, by an arrow "L", this occurring with an audible click, as the flange 46 hits the proximal wall of the housing 12, the spring 42, as shown in FIG. 5, by the pushing of the proximal end 22 of the carriage shaft 20 out of the proximal opening 18 in the housing 12. During the rearward travel of the carriage shaft 20, the needle assembly 30 to which the carriage shaft 20 is engaged, is also pulled proximally (rearwardly) by the first compressive spring 42, as depicted in FIG. 5.

Upon the encountering of the void or epidural space, the needle 30 no longer feels the resistance to its advance and retracts as aforementioned.

FIG. 6 shows the housing 12 and its enclosed/attached needle 30 being removed from the cannula 24, to facilitate delivery of medicaments (or other catheters or medical devices) through the cannula 24 after the distal end of the needle 30 has been removed therefrom. Additionally, the cannula 24 itself, 28 could also be directed further into the body duct.

The valve member 110, as aforementioned, can then be closed to await need for re-opening of the cannula 24 for introduction of a medical device such such as an endoscope, or fluid therethrough. The valve 110 could be replaced by a duckbill valve or a soft, penetrable material with a slit therethrough, not shown. The side valve 120 in the hub assembly also permits supplemental fluid introduction capabilities through the cannula 24 also.

Thus, what has been shown and described is a unique needle device suitable particularly for veress-type procedures, which permits single handed advance into body tissue, and when the needle (trocar) upon entering an body space and sensing no resistance to further forward advance, minutely advances on its own, well within distance limitations of small body space, only to trigger its own immediate retraction, removing the cutting and piercing component from exposure, presenting to that space a cannula tip for subsequent adaptation to a medical device on medicament supply source upon removal of the needle (trocar) and drive assembly from the cannula shaft.

I claim:

1. A needle device for the delivery of medical devices, insuflation or medicaments, comprising:
   an elongated housing;
   a reciprocable hollow needle arranged in a cannula, said cannula attached to the distal end of said housing; and
   a valve arrangement disposed about said hollow needle in the proximal end of said cannula, arranged to be closable upon the retraction of said reciprocable hollow needle from said cannula; including an arrangement of compressable and releasable springs disposed within said housing and attached to said hollow needle so as to bias said hollow needle therefrom; and a detent assembly to actuate retraction of said hollow needle within said cannula upon a decrease in pressure upon said needle as it is being advanced into a space or potential space.

2. A needle device as recited in claim 1, wherein said valve arrangement comprises a base and a cap connectively associated about said hollow needle at the proximal end of said cannula.

3. A needle device as recited in claim 2, wherein said cap is rotatable with respect to said base to effectuate closing of said valve after said needle has been withdrawn therefrom.

4. A needle device as recited in claim 3, wherein a valve member is pivotable from a first open position about a central bore in said base and a second closed position covering said central bore in said base.

5. A needle device as recited in claim 4, wherein said cap and said valve member are engaged so as to effectuate pivoting of said valve member about a pivot axis when said cap is rotated with respect to said base.

6. A needle device as recited in claim 2, wherein said cap is matingly engaged to the distal end of said housing, said cap and said base and said needle being in coaxial alignment.

7. A needle device for delivery of medical devices, insuflation, or medicaments, comprising:

a housing;

a reciprocable hollow needle having a proximal end and a distal end with a lumen therebetween, said proximal end secured within said housing;

a cannula having a bore containing said needle, said cannula having a proximal end and a distal end, said cannula having a valve arrangement on its proximal end, said proximal end being attached to the distal end of said housing; and said valve arrangement having a valve means movably disposed between an open position in coaxial alignment with said valve member closes off said bore of said cannula, and a cap and a base arranged at the proximal end of said cannula, each having a bore therethrough in alignment with said bore therein, whereby rotation of said cap with respect to said base after said needle is withdrawn from said cannula, effectuates pivotal motion of said valve to close off said bore.

8. A needle device as recited in claim 7, wherein said housing has means for retracting said needle into said housing; and an indicator means on the proximal end of said housing to visually signal the retraction of said needle with respect to said cannula and said housing, to indicate the sensing of a void into which said device has been advanced.

9. A needle device for accessing an internal body space, comprising:

an elongated housing having a distal and a proximal end;

a cannula arranged on the distal end of said housing;

a needle reciprocably movable within said housing and said cannula, and retractable from said cannula;

a hub arranged at the proximal end of said cannula by which said cannula is attached to said housing, said hub having a bore extending therethrough, and into said cannula, for receipt of said needle therethrough; and a valve for opening and closing the proximal end of the bore of said cannula when said needle is withdrawn therefrom; said hub being comprised of a cap and a base which are coaxial with one another and are rotatable with respect to one another, which rotation effects a pivoting of a valve across said bore in the absence of a needle therein.

10. A needle device as recited in claim 9, wherein said valve comprises a valve member pivotable on a disc of said base, said valve member having means to engage with said cap and pivot in response to rotation thereof.

11. A needle device as recited in claim 10, wherein said housing has a carriage extending therethrough, said carriage having a longitudinally extending bore therethrough to permit the passage of an optical device or medicaments through said housing while said housing is still attached to said cannula.

12. A needle device as recited in claim 11, wherein said base has a side valve arranged in therein, with a conduit in fluid communication with said bore in said needle to permit insuflation of a patient attached thereto.

13. A needle device as recited in claim 9, wherein said valve is openable by the pushing of a needle therethrough.

14. A method of delivering a medical device, insuflation, or medicaments into a body space, comprising the steps of;

advancing into a body space a needle device having a housing with a hollow needle at the distal end thereof said hollow needle arranged within a cannula;

puncturing a body space by said hollow needle which extends distally beyond the distal end of said cannula; and retracting said hollow needle proximally upon said hollow needle losing resistance to forward or distal advance in a body; and arranging a side valve in said base, said side valve being in fluid communication with said bore in said hollow needle, for the delivery of medicaments therethrough.

15. The method of claim 14, including the step of:

inserting an optical device through said bore of said carriage and said hollow needle so as to visualize the medical procedure of said puncture process.

16. The method of claim 14, including the step of:

inserting a biopsy device through said bore of said carriage and said hollow needle so as to permit the taking of tissue samples therewith.

17. The method of claim 14, including the step of;

removing said hollow needle and said housing from said cannula; and closing a valve at the proximal end of said cannula to seal access to said body space.

18. The method of claim 17, including the steps of;

rotating a cap and a base arranged at the proximal end of said cannula to effectuate pivotal motion of a valve member to open or close access to body space thereby.

19. The method of claim 14, including the step of:

advancing a medicament into said cannula through a side valve therein.

* * * * *